US008293928B2

(12) United States Patent
Drysdale

(10) Patent No.: US 8,293,928 B2
(45) Date of Patent: Oct. 23, 2012

(54) FLUORINATED 4-OXO-CHROMAN-7-CARBOXYLATES

(75) Inventor: Neville Everton Drysdale, Newark, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 164 days.

(21) Appl. No.: 12/873,392

(22) Filed: Sep. 1, 2010

(65) Prior Publication Data

US 2011/0213166 A1    Sep. 1, 2011

Related U.S. Application Data

(60) Provisional application No. 61/239,096, filed on Sep. 2, 2009.

(51) Int. Cl.
*C07D 311/00* (2006.01)
(52) U.S. Cl. ........................................................ 549/401
(58) Field of Classification Search .................. 549/401
See application file for complete search history.

(56) References Cited

U.S. PATENT DOCUMENTS

| | | | |
|---|---|---|---|
| 4,219,625 A | 8/1980 | Mares et al. | |
| 4,841,093 A | 6/1989 | Tamaru et al. | |
| 5,091,456 A | 2/1992 | Rodini | |
| 5,104,961 A | 4/1992 | Muller | |
| 5,243,019 A | 9/1993 | Takeda et al. | |
| 5,349,093 A | 9/1994 | Oka et al. | |
| 5,468,882 A | 11/1995 | Schohe-Loop et al. | |
| 5,756,814 A | 5/1998 | Lin et al. | |
| 6,734,227 B2 | 5/2004 | Jing et al. | |
| 6,790,898 B2 | 9/2004 | Lee et al. | |
| 6,960,642 B2 | 11/2005 | Jariwala et al. | |
| 7,202,324 B2 | 4/2007 | Kim et al. | |
| 7,446,127 B2 | 11/2008 | Choi et al. | |
| 7,825,280 B2 | 11/2010 | Saegusa et al. | |
| 2002/0042526 A1 | 4/2002 | Piscopio et al. | |
| 2003/0001130 A1 | 1/2003 | Qiu | |
| 2004/0235685 A1 | 11/2004 | Russo et al. | |
| 2008/0020148 A1 | 1/2008 | Klein et al. | |
| 2008/0039558 A1 | 2/2008 | Lazzari et al. | |

FOREIGN PATENT DOCUMENTS

| | | |
|---|---|---|
| EP | 1616849 A2 | 1/2006 |
| JP | 62197419 A | 9/1987 |
| JP | 62205181 A | 9/1987 |
| JP | 1249747 A | 11/1989 |
| JP | 5294903 A | 11/1993 |
| JP | 1017522 A | 1/1998 |
| JP | 2005120001 A | 5/2005 |
| KR | 1020030046554 A | 6/2003 |
| KR | 1020040006591 A | 1/2004 |
| WO | 9967304 A1 | 12/1999 |
| WO | 2006043501 A1 | 4/2006 |

OTHER PUBLICATIONS

Co-pending U.S. Appl. No. 12/873,396, Neville Everton Drysdale, filed Sep. 1, 2010.
Co-pending U.S. Appl. No. 12/873,402, Neville Everton Drysdale, filed Sep. 1, 2010.
Co-pending U.S. Appl. No. 12/873,418, Neville Everton Drysdale, filed Sep. 1, 2010.
Co-pending U.S. Appl. No. 12/873,423, Neville Everton Drysdale, filed Sep. 1, 2010.
Co-pending U.S. Appl. No. 12/873,428, Neville Everton Drysdale, filed Sep. 1, 2010.
Feiring, A.E. et al., Aromatic Monomers with Pendant Fluoroalkylsulfonate and Sulfonimide Groups, Journal of Fluorine Chemistry 105(2000), pp. 129-135.
ASTM International, Designation: E29-08, Standard Practice for Using Significant Digits in Test Data to Determine Conformance with Specifications, pp. 1-5.
International Search Report, Related PCT International Application No. PCT/US2010/047514 Mailed May 18, 2011 (Neville Everton Drysdale et al., Filed Sep. 1, 2010).
International Search Report, Related PCT International Application No. PCT/US2010/047480 Mailed May 18, 2011 (Neville Everton Drysdale et al., Filed Sep. 1, 2010).
Related PCT International Application No. PCT/US2010/049962 (Neville Everton Drysdale, Filed Sep. 23, 2010).
International Search Report, Related PCT International Application No. PCT/US2010/047473 Mailed Mar. 17, 2011 (Neville Everton Drysdale et al., Filed Sep. 1, 2010).
International Search Report, Related PCT International Application No. PCT/US2010/047492 Mailed May 31, 2011 (Neville Everton Drysdale et al., Filed Sep. 1, 2010).
JP2005-120001, Machine Translation, Thomson Innovation (www.thomsoninnovation.com, Sep. 26, 2011).
JP62-197491A, Machine Translation of Abstract Only (www.worldwide.espacenet.com, Sep. 26, 2011).
JP62-205181A, Machine Translation of Abstract Only (www.worldwide.espacenet.com, Sep. 26, 2011).
JP12-49747, Machine Translation of Abstract Only (www.worldwide.espacenet.com, Sep. 26, 2011).
JP52-94903A, Machine Translation of Abstract Only (www.worldwide.espacenet.com, Sep. 26, 2011).

*Primary Examiner* — Nizal Chandrakumar

(57) ABSTRACT

The present invention is directed to compositions comprising fluorinated 4-oxo-chroman-carboxylates, particularly fluorinated 4-oxo-chroman-7-carboxylate, and a process for making the same. The compounds are useful as intermediates in the production of agricultural chemicals, and also as chain terminators in condensation polymerization reactions, particularly when it is desired to provide a polymer having a relatively low surface energy.

16 Claims, No Drawings

FLUORINATED 4-OXO-CHROMAN-7-CARBOXYLATES

FIELD OF THE INVENTION

The present invention is directed to compositions comprising fluorinated 4-oxo-chroman-carboxylates and methods for making the same. The compounds are useful as intermediates in the production of agricultural chemicals, and also as chain terminators in polyester polymerization.

BACKGROUND

Fluorinated materials have many uses. In particular, they are used in the in polymer-related industries, and, more particularly, in fiber-related industries, to impart soil, water and oil resistance, and improved flame retardancy. Generally, these materials are applied as a topical treatment, but their effectiveness decreases over time due to material loss via wear and washing. They can also find use in agricultural end-uses such as herbicides, fungicides and the like.

There is a need to provide materials that have improved soil and oil resistance in general, as well as materials that maintain such properties over time. By incorporating fluorinated aromatic diesters into polymer backbones, more permanent soil, water and oil resistance, as well as improved flame retardancy, can be achieved.

SUMMARY OF THE INVENTION

One aspect of the present invention is a fluorinated 4-oxo-chroman-carboxylate or carboxylic acid represented by structure (I):

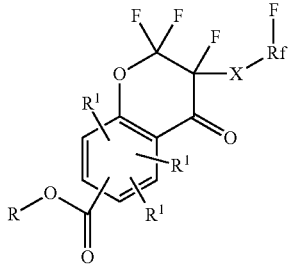

wherein:
R is H, $C_1$-$C_{10}$ alkyl, $C_5$-$C_{15}$ aryl, or $C_6$-$C_{20}$ arylalkyl;
each $R^1$ is independently $C_1$-$C_{10}$ alkyl, $C_5$-$C_{15}$ aryl, $C_6$-$C_{20}$ arylalkyl, or halogen;
X is O or $CF_2$; and
Rf is $(CF_2)_n$, wherein n is an integer within the range of 1-10

Another aspect of the present invention is a process, comprising combining in a reaction vessel a hydroxyaromatic diester or diacid with a perfluorovinyl compound in the presence of a basic catalyst to form a reaction mixture, sealing the reaction vessel, and stirring the reaction mixture under the autogenous pressure of the perfluorovinyl compound to effect reaction; wherein the hydroxy aromatic diester or diacid is represented by the structure (II)

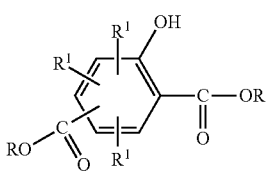

wherein R is H, $C_1$-$C_{10}$ alkyl, $C_5$-$C_{15}$ aryl, or $C_6$-$C_{20}$ arylalkyl;
each $R^1$ is independently $C_1$-$C_{10}$ alkyl, $C_5$-$C_{15}$ aryl, $C_6$-$C_{20}$ arylalkyl, or halogen;
and wherein the perfluorovinyl compound is represented by the structure (III)

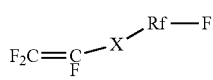

wherein X is O or $CF_2$; and
Rf is $(CF_2)_n$, and wherein n is an integer within the range of 1-10

DETAILED DESCRIPTION

Disclosed herein are fluorinated 4-oxo-chroman-carboxylates and processes for making the compounds. The compounds have the formula:

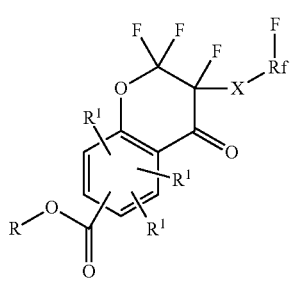

wherein:
each R is independently H, $C_1$-$C_{10}$ alkyl, $C_5$-$C_{15}$ aryl, or $C_6$-$C_{20}$ arylalkyl;
each $R^1$ is independently H, $C_1$-$C_{10}$ alkyl, $C_5$-$C_{15}$ aryl, $C_6$-$C_{20}$ arylalkyl, or halogen;
each X is independently O or $CF_2$; and
each Rf is independently $(CF_2)_n$, wherein each n is independently an integer within the range of 1-10.

The substituents on the benzene ring in the above formulas can be attached to the benzene ring at any point, thus making it possible to have ortho-, meta- and para-substituents as defined above.

In one embodiment of the compound R is H.

In an alternative embodiment of the compound, R is $C_1$-$C_{10}$ alkyl, $C_5$-$C_{15}$ aryl, or $C_6$-$C_{20}$ arylalkyl. In a further embodiment, R is methyl.

In one embodiment of the compound $R^1$ is H.

In one embodiment of the compound, X is O. In an alternative embodiment of the compound, X is $CF_2$.

In one embodiment of the compound Rf is $CF_2$. In an alternative embodiment of the compound, $(CF_2)_2$.

In one embodiment of the compound, the carboxylate group is located at position 7.

In one embodiment of the compound R is methyl, each $R^1$ is H, X is O and n=2.

In another aspect, the invention provides a process comprising combining in a reaction vessel a hydroxyaromatic diester or diacid with a perfluorovinyl compound in the presence of a basic catalyst to form a reaction mixture, sealing the reaction vessel, and stirring the reaction mixture under the autogenous pressure of the perfluorovinyl compound to effect reaction; wherein the hydroxy aromatic diester or diacid is represented by the structure (II) The reaction can be performed at elevated temperature.

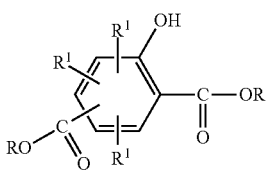

wherein R is H, $C_1$-$C_{10}$ alkyl, $C_5$-$C_{15}$ aryl, or $C_6$-$C_{20}$ arylalkyl;
each $R^1$ is independently $C_1$-$C_{10}$ alkyl, $C_5$-$C_{15}$ aryl, $C_6$-$C_{20}$ arylalkyl, or halogen;
and wherein the perfluorovinyl compound is represented by the structure (III)

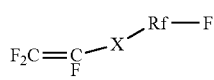

wherein X is O or $CF_2$; and
Rf is $(CF_2)_n$, and wherein n is an integer within the range of 1-10

Suitable solvents include, but are not limited to, dimethyl formamide, carbon tetrabromide, or tetrahydrofuran Any basic catalyst that is capable of deprotonating phenol is suitable. Suitable catalysts include but are not limited to potassium t-butoxide, potassium carbonate, or sodium carbonate, The progress of the reaction can be monitored by thin layer chromatography or proton NMR. The reaction can be terminated by the addition of acid such as HCl. In one embodiment of the compound of the process the process further comprises diluting the reaction product with a solvent (typically methylene chloride, chloroform, carbon tetrachloride, THF or 1,4-dioxane) followed by washing with additional acid and water. In a further embodiment, the thus washed product is dried, concentrated under reduced pressure, and dried again under vacuum. The resulting final product can be isolated by any convenient method, such as, for example, column chromatography.

In one embodiment the hydroxy aromatic diester or diacid is a hydroxyaromtic diester. In a further embodiment, the hydroxy aromatic diester is dimethyl 2-hydroxy terephthalate.

In one embodiment of the process R is H.

In an alternative embodiment of the process, R is $C_1$-$C_{10}$ alkyl, $C_5$-$C_{15}$ aryl, or $C_6$-$C_{20}$ arylalkyl. In a further embodiment of the process R is methyl.

In one embodiment of the process $R^1$ is H.

In one embodiment of the process, X is O. In an alternative embodiment of the process, X is $CF_2$.

In one embodiment of the process Rf is $CF_2$. In an alternative embodiment of the process, Rf is $(CF_2)_2$.

In one embodiment of the process R is methyl, each $R^1$ is H, X is $CF_2$, and Rf is $(CF_2)_2$, and the aromatic diester is 2-hydroxy dimethyl terephthallate.

EXAMPLES

The following chemicals and reagents were used as received from Sigma-Aldrich, Milwaukee, Wis.:
potassium t-butoxide
dimethyl formamide
carbon tetrabromide (tetrabromomethane)
1,4-dimethyl-2-hydroxy terephthalate
methylene chloride Perfluoroprop-1-ene was used as received from SynQuest Labs., Alachua, Fla.:

Example 1

(Methyl 2,2,3-trifluoro-4-oxo-3-(trifluoromethyl) chroman-7-carboxylate)

Chemical Formula: $C_{12}H_6F_6O_4$
Exact Mass: 328.02
Molecular Weight: 328.16

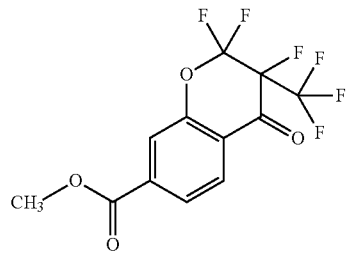

methyl 2,2,3-trifluoro-4-oxo-3-
(trifluoromethyl)chroman-7-carboxylate

In a dry box, dimethyl formamide (50.00 mL) and carbon tetrabromide were added to a reaction flask equipped with a stirring bar. To this solution in the reaction flask was added 1,4-dimethyl-2-hydroxy terephthalate (5.25 g, 0.025 mol) to form a homogeneous reaction solution. To this homogeneous reaction solution in the reaction flask was added potassium t-butoxide (0.77 g, 0.0069 mol). Perfluoroprop-ene (9.375 g, 0.0625 mol) was then added to the reaction flask to form a reaction mixture. The reaction mixture was stirred for 24 hours. The reaction was terminated by the addition of 2 mL of 10% HCl to the reaction mixture. The resulting reaction solution was diluted with methylene chloride (250 mL) and then washed with 10% HCl (2×100 mL) and then with water (3×100 mL). The resulting reaction product was then dried over anhydrous sodium sulfate, concentrated at reduced pressure and then dried under vacuum. Column chromatography afforded the desired product, methyl 2,2,3-trifluoro-4-oxo-3-(trifluoromethyl)chroman-7-carboxylate), as a white solid (0.71 g, 8.6% yield, Rf: ~0.50 methylene chloride/hexane 91:1)).

Example 2

(Methyl 2,2,3-trifluoro-4-oxo-3-(trifluoromethyl) chroman-7-carboxylate)

Chemical Formula: $C_{12}H_6F_6O_4$
Exact Mass: 328.02
Molecular Weight: 328.16

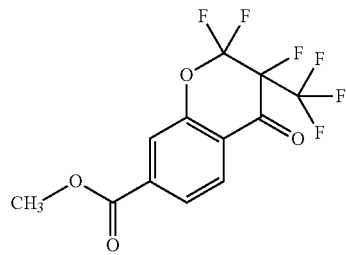

methyl 2,2,3-trifluoro-4-oxo-3-
(trifluoromethyl)chroman-7-carboxylate

In a dry box, 1,4-dimethyl-2-hydroxy terephthalate (5.25 g, 0.025 mol) was weighed into a round bottom reaction flask, equipped with a stirring bar. To this material in the reaction flask was added dimethyl formamide (250.00 mL) and potassium t-butoxide (0.77 g, 0.0069 mol), forming a reaction mixture. To this reaction mixture was added perfluoroprop-1-ene (9.375 g, 0.0625 mol). The resulting reaction mixture was stirred for ~24 hours. The reaction was terminated by the addition of 10% HCl (2 mL). The resulting reaction product was diluted with methylene chloride and then washed with 10% HCl (2×100 mL) and then with water (2×100 mL), forming an organic phase and an aqueous phase. The s separated organic phase was dried over anhydrous sodium sulfate, filtered and then concentrated at reduced pressure and then column chromatographed to 3.71 (45.24% yield) of the desired material, identified by NMR, as methyl 2,2,3-trifluoro-4-oxo-3-(trifluoromethyl)chroman-7-carboxylate.

What is claimed is:

1. A composition comprising a fluorinated 4-oxo-chroman-carboxylate or carboxylic acid represented by structure (I)

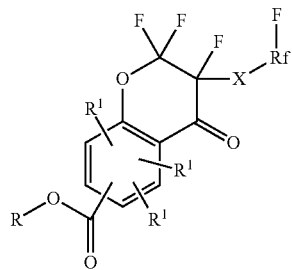

wherein:
R is $C_1$-$C_{10}$ alkyl, $C_5$-$C_{15}$ aryl, or $C_6$-$C_{20}$ arylalkyl;
each $R^1$ is independently $C_1$-$C_{10}$ alkyl, $C_5$-$C_{15}$ aryl, $C_6$-$C_{20}$ arylalkyl, or halogen;
X is $CF_2$; and
Rf is $(CF_2)_n$, wherein n is an integer within the range of 0-10.

2. The composition of claim 1 wherein R is methyl.
3. The composition of claim 1 wherein each $R^1$ is H.
4. The composition of claim 1 wherein X is $CF_2$.
5. The composition of claim 1 wherein Rf is $(CF_2)_2$.
6. The composition of claim 1 wherein the fluorinated 4-oxo-chroman-carboxylate or carboxylic acid is a fluorinated 4-oxo-chroman-carboxylate.
7. The composition of claim 6 wherein the fluorinated 4-oxo-chroman-carboxylate is a fluorinated 4-oxo-chroman-7-carboxylate.
8. The composition of claim 1 wherein R is methyl, each $R^1$ is H, X is $CF_2$, Rf is $(CF_2)_2$, and the fluorinated 4-oxo-chroman-carboxylate or carboxylic acid is a fluorinated 4-oxo-chroman-carboxylate.

9. A process comprising combining in a reaction vessel a hydroxyaromatic diester or diacid with a perfluorovinyl compound in the presence of a basic catalyst to form a reaction mixture, sealing the reaction vessel, and stirring the reaction mixture under the autogenous pressure of the perfluorovinyl compound to produce a fluorinated 4-oxo-chroman-carboxylate or carboxylic acid represented by structure (I) of claim 1; wherein the hydroxy aromatic diester or diacid is represented by the structure (II)

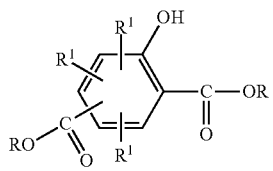

wherein R is $C_1$-$C_{10}$ alkyl, $C_5$-$C_{15}$ aryl, or $C_6$-$C_{20}$ arylalkyl;
each $R^1$ is independently $C_1$-$C_{10}$ alkyl, $C_5$-$C_{15}$ aryl, $C_6$-$C_{20}$ arylalkyl, or halogen;
and wherein the perfluorovinyl compound is represented by the structure (III)

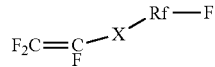

wherein X is $CF_2$; and
Rf is $(CF_2)_n$, and wherein n is an integer within the range of 0-10.

10. The process of claim 9 wherein R is methyl.
11. The process of claim 9 wherein each $R^1$ is H.
12. The process of claim 9 wherein X is $CF_2$.
13. The process of claim 9 wherein Rf is $(CF_2)_2$.
14. The process of claim 9 wherein the hydroxy aromatic diester or diacid is a hydroxy aromatic diester.
15. The process of claim 9 wherein the hydroxyaromatic diester is dimethyl 2-hydroxy terephthalate.
16. The process of claim 9 wherein X is $CF_2$, and the hydroxyaromatic diester or diacid is dimethyl 2-hydroxy terephthalate.

* * * * *